(12) United States Patent
Bray

(10) Patent No.: US 7,578,833 B2
(45) Date of Patent: Aug. 25, 2009

(54) BONE FASTENER ASSEMBLY FOR BONE RETENTION APPARATUS

(75) Inventor: Robert S. Bray, Studio City, CA (US)

(73) Assignee: Dr. Robert S. Bray, Jr., Studio City, CA (US)

( * ) Notice: Subject to any disclaimer, the term of this patent is extended or adjusted under 35 U.S.C. 154(b) by 545 days.

(21) Appl. No.: 11/011,794

(22) Filed: Dec. 13, 2004

(65) Prior Publication Data

US 2006/0149231 A1     Jul. 6, 2006

(51) Int. Cl.
    *A61B 17/70*     (2006.01)
(52) U.S. Cl. ..................... 606/246; 606/267
(58) Field of Classification Search ............. 606/59–61, 606/72–73; 623/16.11, 17.11
    See application file for complete search history.

(56) References Cited

U.S. PATENT DOCUMENTS

| | | | |
|---|---|---|---|
| 4,648,388 A | 3/1987 | Steffee | |
| 4,719,905 A | 1/1988 | Steffee | |
| 5,002,542 A | 3/1991 | Frigg | |
| 5,030,220 A | 7/1991 | Howland | |
| 5,129,900 A | 7/1992 | Asher et al. | |
| 5,176,680 A * | 1/1993 | Vignaud et al. | 606/61 |
| 5,254,118 A | 10/1993 | Mirkovic | |
| 5,282,862 A * | 2/1994 | Baker et al. | 606/61 |
| 5,300,073 A * | 4/1994 | Ray et al. | 606/61 |
| 5,312,404 A | 5/1994 | Asher et al. | |
| 5,344,422 A | 9/1994 | Frigg | |
| 5,352,226 A * | 10/1994 | Lin | 606/61 |
| 5,380,323 A | 1/1995 | Howland | |
| 5,380,325 A * | 1/1995 | Lahille et al. | 606/61 |
| 5,466,237 A | 11/1995 | Byrd, III et al. | |
| 5,474,551 A | 12/1995 | Finn et al. | |
| 5,476,463 A | 12/1995 | Boachie-Adjei et al. | |

(Continued)

FOREIGN PATENT DOCUMENTS

DE     19512709 A1     10/1996

(Continued)

OTHER PUBLICATIONS

EP Search Report (05445028.3 1263/1596060) dated Aug. 22, 2008.

(Continued)

*Primary Examiner*—Eduardo C Robert
*Assistant Examiner*—David Comstock
(74) *Attorney, Agent, or Firm*—Pearne & Gordon LLP

(57) ABSTRACT

An assembly, comprising a bone fastener, an adjusting member and a securing fastener for fastening an appliance to a bone body so that a plurality of the bone fastener assemblies and the appliance constitute an apparatus that retain a plurality of bone bodies. Each fastener has an attaching portion for attaching the bone fastener to a bone body, a supporting portion for supporting the adjusting member for universal movement relative to the supporting portion, and a securing portion for securing the bone fastener to the fastener. The fastener has a first end that passes through an aperture in the appliance and an opening in the adjusting member and is secured to the securing portion of the bone fastener. A second end of the fastener has a bearing surface that adjustably bears against the appliance in opposition to an engaging surface of the adjusting member that engages the appliance.

5 Claims, 3 Drawing Sheets

U.S. PATENT DOCUMENTS

| | | | |
|---|---|---|---|
| 5,478,340 A | 12/1995 | Kluger | |
| 5,545,166 A | 8/1996 | Howland | |
| 5,562,661 A | 10/1996 | Yoshimi et al. | |
| 5,569,247 A | 10/1996 | Morrison | |
| 5,591,166 A | 1/1997 | Bernhardt et al. | |
| 5,628,740 A | 5/1997 | Mullane | |
| 5,649,926 A | 7/1997 | Howland | |
| 5,676,665 A * | 10/1997 | Bryan | 606/61 |
| 5,688,275 A | 11/1997 | Koros et al. | |
| 5,725,528 A | 3/1998 | Errico et al. | |
| 5,733,286 A | 3/1998 | Errico et al. | |
| 5,735,850 A | 4/1998 | Baumgartner et al. | |
| 5,735,851 A | 4/1998 | Errico et al. | |
| 5,741,255 A | 4/1998 | Krag et al. | |
| 5,743,907 A | 4/1998 | Asher et al. | |
| 5,752,957 A | 5/1998 | Ralph et al. | |
| 5,776,134 A | 7/1998 | Howland | |
| 5,800,435 A | 9/1998 | Errico et al. | |
| 5,938,663 A | 8/1999 | Petreto | |
| 5,947,965 A | 9/1999 | Bryan | |
| 5,961,518 A | 10/1999 | Errico et al. | |
| 5,976,135 A | 11/1999 | Sherman et al. | |
| 5,984,924 A | 11/1999 | Asher et al. | |
| 6,015,409 A | 1/2000 | Jackson | |
| 6,030,388 A | 2/2000 | Yoshimi et al. | |
| 6,050,997 A | 4/2000 | Mullane | |
| 6,080,156 A | 6/2000 | Asher et al. | |
| 6,083,226 A | 7/2000 | Fiz | |
| 6,106,526 A | 8/2000 | Harms et al. | |
| 6,123,706 A | 9/2000 | Lange | |
| 6,146,383 A | 11/2000 | Studer et al. | |
| 6,179,838 B1 | 1/2001 | Fiz | |
| 6,187,005 B1 | 2/2001 | Brace et al. | |
| 6,231,575 B1 | 5/2001 | Krag | |
| 6,267,765 B1 | 7/2001 | Taylor et al. | |
| 6,273,914 B1 | 8/2001 | Papas | |
| 6,280,443 B1 | 8/2001 | Gu et al. | |
| 6,299,614 B1 | 10/2001 | Kretschmer et al. | |
| 6,309,390 B1 | 10/2001 | Le Couedic et al. | |
| 6,314,938 B1 | 11/2001 | McCreery et al. | |
| 6,328,739 B1 | 12/2001 | Liu et al. | |
| 6,413,257 B1 | 7/2002 | Lin et al. | |
| 6,432,109 B1 | 8/2002 | Letendart et al. | |
| 6,451,021 B1 | 9/2002 | Ralph et al. | |
| 6,595,993 B2 | 7/2003 | Donno et al. | |
| 6,623,485 B2 | 9/2003 | Doubler et al. | |
| 6,673,074 B2 | 1/2004 | Shluzas | |
| 6,706,045 B2 | 3/2004 | Lin et al. | |
| 6,736,816 B2 | 5/2004 | Ritland | |
| 6,755,830 B2 | 6/2004 | Minfelde et al. | |
| 6,786,907 B2 * | 9/2004 | Lange | 606/250 |
| 2002/0169450 A1 * | 11/2002 | Lange | 606/61 |
| 2003/0045878 A1 | 3/2003 | Petit et al. | |
| 2003/0055426 A1 | 3/2003 | Carbone et al. | |
| 2003/0093078 A1 | 5/2003 | Ritland | |

FOREIGN PATENT DOCUMENTS

| | | |
|---|---|---|
| EP | 0364118 | 1/1993 |
| EP | 1394404 | 3/2004 |
| FR | 2765093 A | 12/1998 |
| JP | 2003322075 | 11/2003 |

OTHER PUBLICATIONS

Supplementary European Search Report Dated May 7, 2009.

* cited by examiner

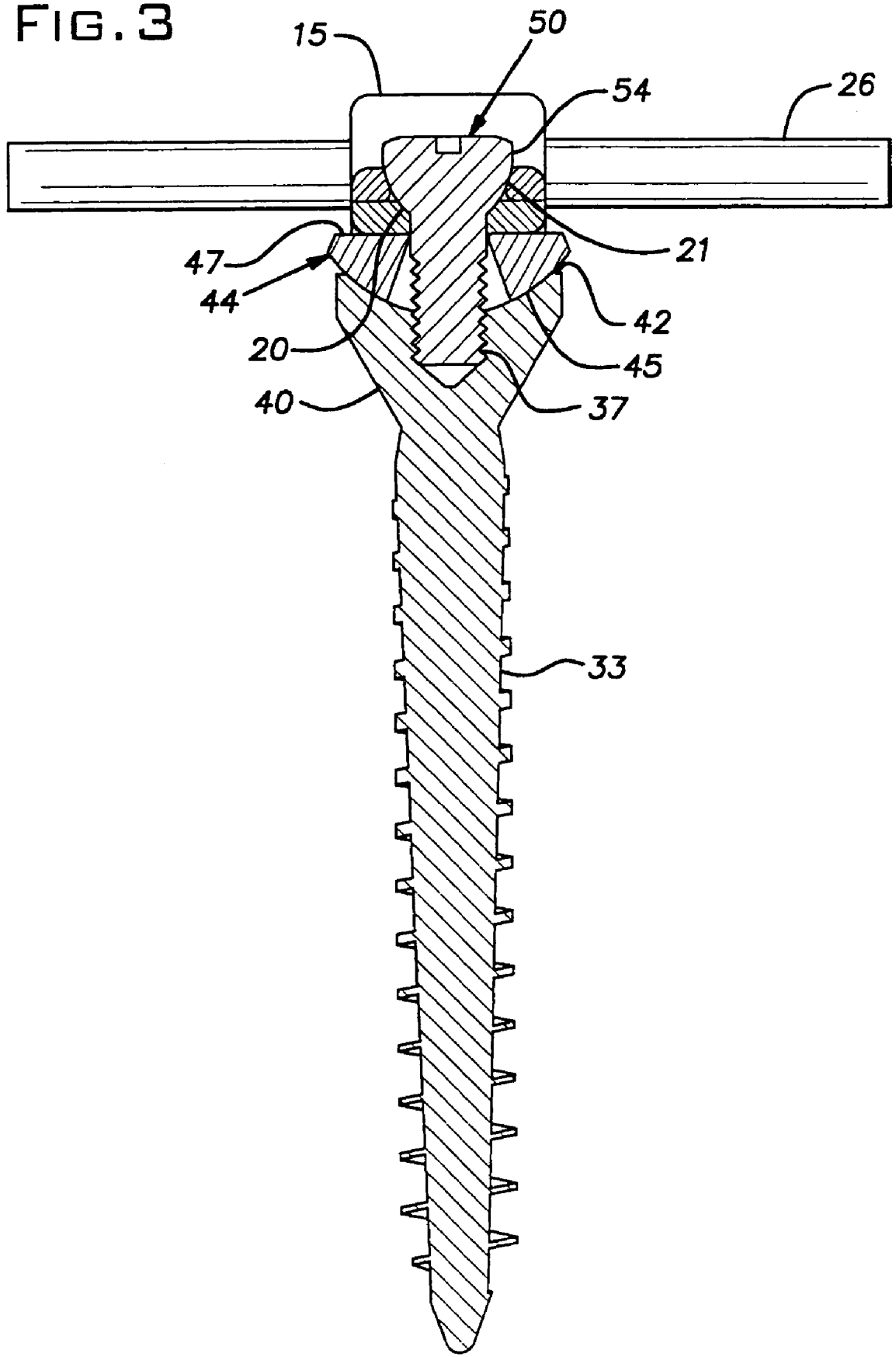

BONE FASTENER ASSEMBLY FOR BONE RETENTION APPARATUS

FIELD OF THE INVENTION

The present invention relates to apparatuses that have utility in connection with the retention of bone bodies in a desired spatial relationship. More particularly, the invention concerns a pedicle screw assembly for an appliance that maintains a desired spatial relationship among the vertebrae of a spine.

BACKGROUND OF THE INVENTION

A variety of devices are known for the fixation, internally or otherwise, of bone bodies in humans and animals. In the case of the internal fixation of the vertebrae of a spinal column, so that the vertebrae are maintained in a desired spatial relationship with respect to one another, the devices often include pedicle screw, or bone fastener, assemblies. These assemblies include a pedicle screw, or bone fastener, that is anchored, typically by a threaded arrangement, into the pedicle of each of the vertebrae that are to be maintained in a desired spatial relationship. One or more appliances such as longitudinal supports, which may comprise plates or rods, that extend longitudinally of the spinal column are connected securely to the pedicle screw assemblies in a manner that allows the vertebrae to be maintained in a desired alignment. In order to achieve the desired stability, the bone fasteners must be attached securely to the vertebrae and connected firmly to the appliance.

The bone fasteners may be connected directly to the rods or plates, or the connection between the bone fasteners and the rods may be accomplished by the use of a connector or coupling member that forms a part of the appliance. In the latter instance, the end of the bone fastener that is not attached to the vertebrae is secured to one end of the coupling member and the other end of the coupling member is secured to the rod or plate.

The secure placement of a rod with a rigid bone fastener, whether or not a coupling member is used, or the placement of a plate between two or more rigid screws is difficult for a variety of reasons. For example, the displacement or angulation of the vertebrae may be such that the rigidity of the bone fastener and/or coupling member, where a coupling member is used, prevents a secure connection from being made among the components of the bone alignment system. Additionally, installation is difficult because the rod or plate must align precisely with all of the bone fasteners.

Although a bend can be made in the rod or plate in order that the bone fasteners be firmly secured to the rod or plate, the possibility exits that stresses can be created that cause the bone bodies or vertebrae to fracture or the screws to loosen over time. This is even the case when rods having a degree of flexibility are used. Thus it is important that bone fastener assemblies be provided that minimize the likelihood of the establishment of undesirable stresses.

SUMMARY OF THE INVENTION

According to one aspect of the invention, a bone fastener assembly comprises a bone fastener, an adjusting member and a securing fastener. The bone fastener has an attaching portion for attaching the bone fastener to a bone or bone part; a supporting portion; and a securing portion. The adjusting member is supported by the supporting portion of the bone fastener and includes an opening extending through it. The opening in the adjusting member is in registration with the securing portion of the bone fastener. The adjusting member also includes an engaging surface that is adapted to engage an appliance adjacent to an aperture in the appliance. The supporting portion of the bone fastener and the adjusting member are configured so that the adjusting member is supported by the supporting portion of the bone fastener for universal movement relative to the supporting portion of the bone fastener. The securing fastener has a first end that is adapted to pass through the aperture in the appliance. The first end of the securing fastener extends through the opening in the adjusting member and is secured to the securing portion of the bone fastener. A second end of the securing fastener has a bearing surface that is adapted to bear against the appliance in opposition to the engaging surface of the adjusting member, whereby the appliance may be securely fastened to the bone fastener.

According to another aspect, the supporting portion of the bone fastener includes a terminal portion and the adjusting member is sized so that the engaging surface of the adjusting member extends beyond the terminal portion of the supporting portion of the bone fastener in the direction of the appliance. With this arrangement, the terminal portion of the supporting portion of the bone fastener may be maintained out of contact with the appliance.

According to still another aspect, the attaching portion of the bone fastener comprises a shank having a longitudinal axis extending from a bottom end to a top end of the shank. The outer portion of the shank has threads that are suitable for attaching the bone fastener to a bone or bone part. In a particular aspect, the supporting portion of the bone fastener is positioned at the top end of the shank. The supporting portion includes a spherical recess in which the supporting portion of the bone fastener supports the adjusting member, and the adjusting member, where it is supported by the supporting portion of the bone fastener, has a complementary spherical surface.

According to yet another aspect, the securing portion of the bone fastener comprises a threaded cavity and the outer portion of the securing fastener includes threads that secure the securing fastener to the threaded cavity of the bone fastener.

According to a further aspect, the opening in the adjusting member extends from a first end at the engaging surface of the adjusting member to a second end that abuts the threaded cavity in the securing portion of the bone fastener. The second end of the opening is larger than the first end of the opening in the adjusting member. According to a particular aspect, the opening in the adjusting member has the shape of a frustrum of a cone.

According to another aspect, the bone fastener assembly fastens the appliance to bone bodies and the apparatus retains the bone bodies in a desired spatial relationship. The apertures in the appliance are located where the appliance is attached to the bone bodies. The bearing surface of the securing fastener has a generally convex configuration that engages a complementary concave surface in the appliance.

According to still another aspect, the appliance comprises a coupling member having a first portion and a second portion and an elongated member such as a rod or plate. The first portion of the coupling member is secured to the bone fastener assembly and the second portion of the coupling member is connected to the elongated member.

According to all the foregoing aspects, the combined rotational and translational degrees of freedom provided by the adjusting member and securing fastener permit the bone fastener to remain firmly fixed but easily attached to the appliance.

BRIEF DESCRIPTION OF THE DRAWINGS

The detailed description of the present invention that follows is presented with reference to the accompanying drawings wherein the same reference numerals denote the same elements in the several views and wherein:

FIG. 3 is a cross-sectional view through the line 3-3 of FIG. 1.

DETAILED DESCRIPTION OF THE INVENTION

Figure 1:
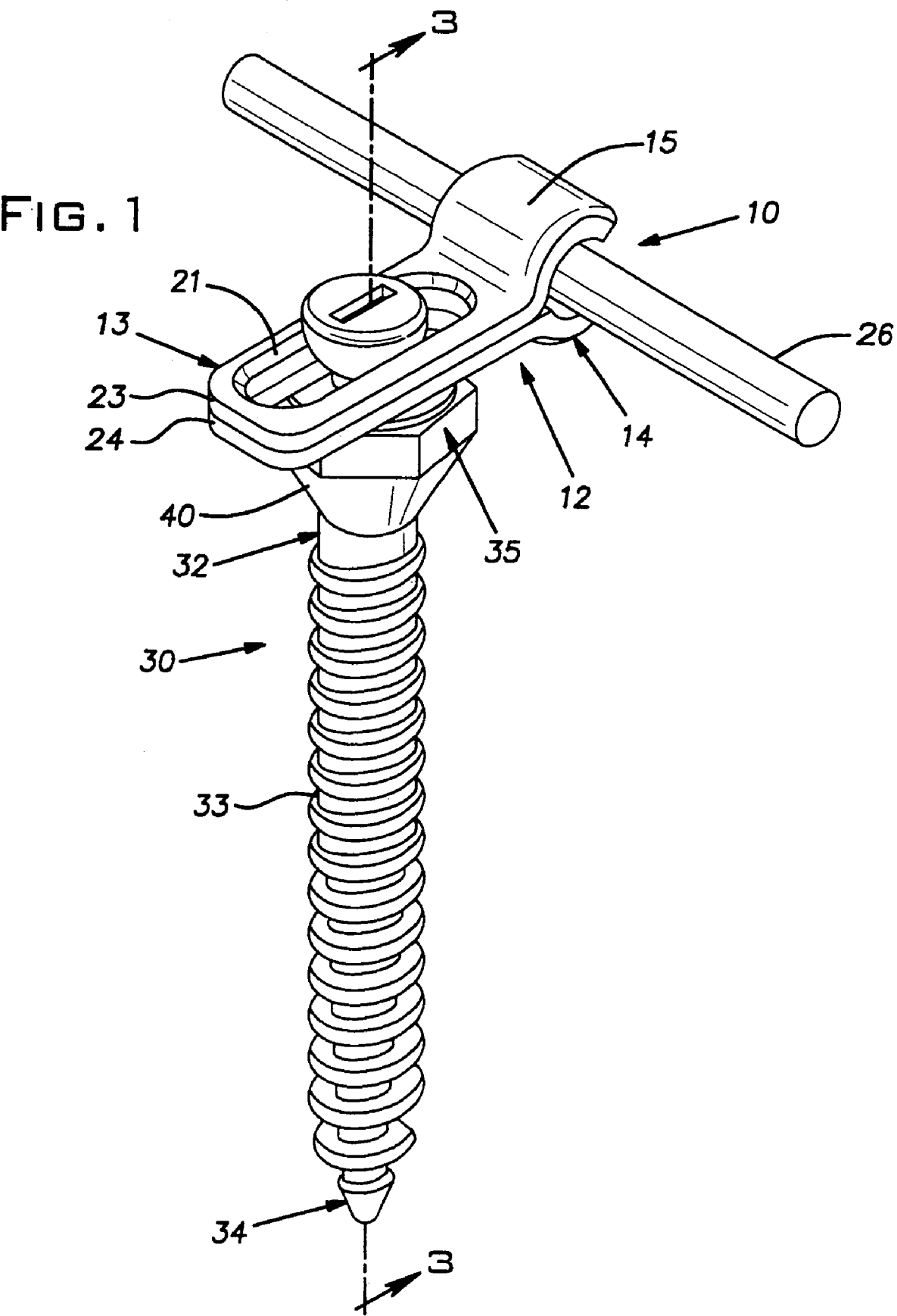
FIG. 1 is a perspective view of an apparatus comprising the bone fastener assembly and appliance of an embodiment of the invention.

Referring first to FIG. 1 of the drawings, there is shown in an assembled state apparatus for use in retaining bone bodies, such as spinal vertebrae, in a desired spatial relationship. The apparatus includes an appliance, indicated generally at 10, for aligning bone bodies, and a bone fastener assembly, indicated generally at 30, for fastening the appliance to one of the bone bodies.

In the embodiment of the invention shown in FIG. 1, the appliance comprises a coupling member, indicated generally at 12, and an elongated member or fixation rod 26. The coupling member 12 has a first portion, indicated generally at 13, that is secured to the bone fastener assembly 30 and a second portion, indicated generally at 14, that is connected to the rod 26. As shown in the Figures, the portion 14 is curved and the portion 13 is flat in comparison to the curved portion. Typically, for the purpose of stabilizing the vertebrae in a spinal column so that the vertebrae are retained in a desired spatial relationship, a respective coupling member 12 and an associated bone fastener assembly 30 secured to the respective coupling member are provided for each of the vertebrae to be stabilized. Each of the coupling members 12 is connected to the rod 26 which serves to retain the vertebrae in a desired spatial relationship.

Figure 2:
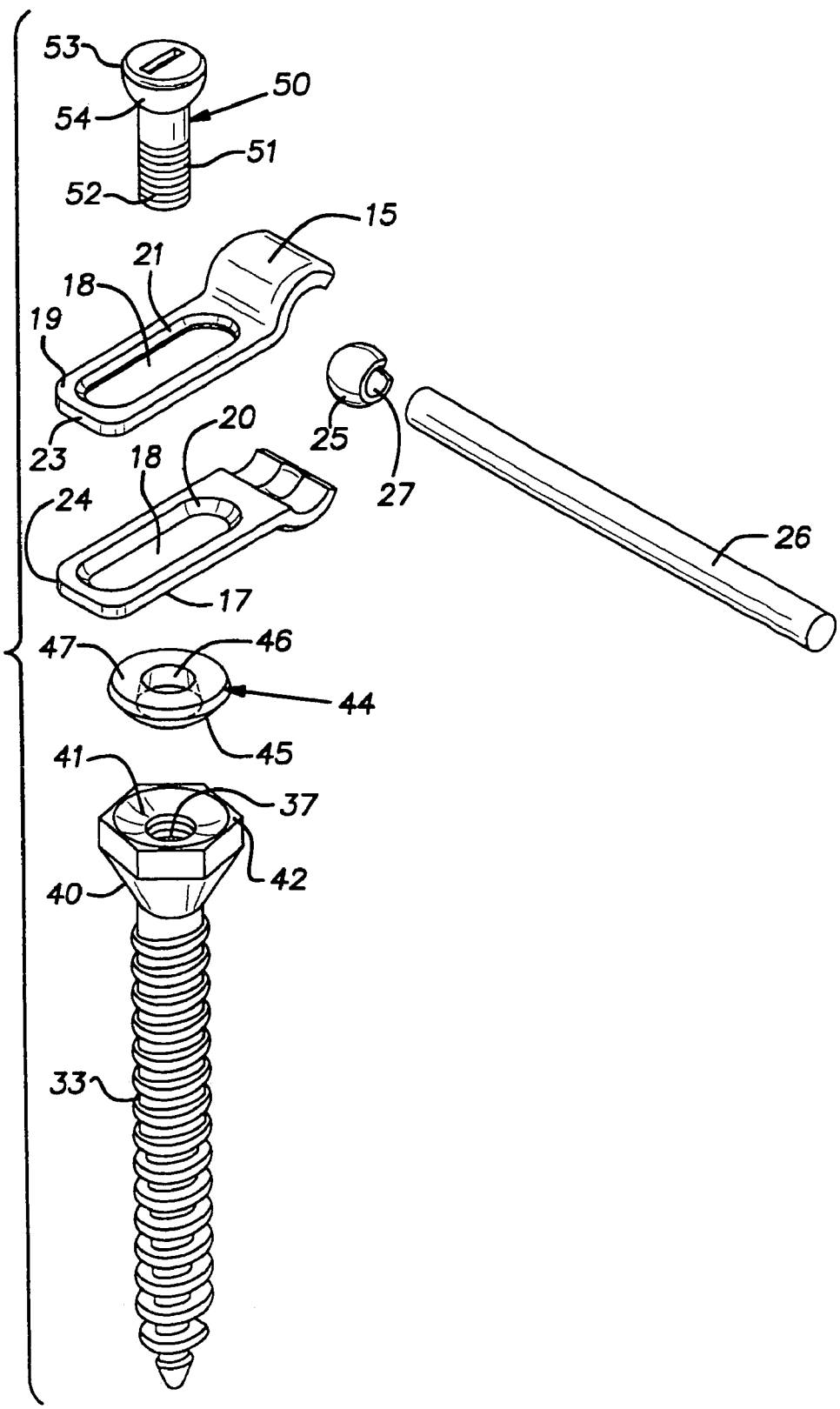
FIG. 2 is an exploded view of the bone fastener and assembly depicted in FIG. 1.

There are a variety of means known in the art for connecting a coupling member, such as the coupling member 12, to a fixation rod, such as rod 26, and many of these known means can be adapted to the apparatus of the present invention. In the embodiment of the invention illustrated in the drawings, the coupling member 12 includes two individual substantially identical halves consisting of a top half 23 and a bottom half 24, which are first and second clamp portions as shown in the Figures. The second portion 14 of each of the top and bottom halves 23 and 24 are inclined away from the first portion 13 of the top and bottom halves, respectively, so as to form a yoke 15. A grommet 25 (spherical outer surface as shown in FIG. 2) is located within curved segments of the first and second clamp portions of the yoke 15, as shown in FIGS. 1 and 2. The inside of the yoke may include a recess in which the spherical grommet 25 is positioned. The rod 26 extends through an opening 27 in the grommet, the opening being equal to or slightly smaller than the diameter of the rod 26 so that the grommet will be in good contact with the rod. The rod 26 is finally secured to the coupling member 12 at such time as the bone fastener assembly 30 is secured to coupling member as is described in further detail below.

Turning now to a description of the bone fastener assembly 30, the bone fastener assembly includes a bone fastener, indicated generally at 32, an adjusting member, indicated generally at 44, and a securing fastener, indicated generally at 50. As shown in the Figures, the adjusting member 44 is annular about its opening 46. As shown in the Figures (and especially FIG. 3 which shows a single and completely extensive material section shading), the bone fastener 32 is monolithic (a unitary or one-piece member). The bone fastener 32 has an attaching portion 33 for attaching the bone fastener to a bone or bone part, such as the pedicle of a vertebra. In the embodiment of the invention shown in the drawings, the attaching portion 33 comprises a shank having a longitudinal axis extending from the bottom end of the shank, indicated generally at 34, to the top end of the shank just before the top end, indicated generally at 35, of the bone fastener. The outer portion of the shank has threads suitable for attaching the bone fastener 32 to a bone or bone part such as the pedicle of a vertebra. Thus, typically as an initial step in a procedure for aligning and retaining spinal vertebrae in a desired spatial relationship, a respective bone fastener 32 is screwed into each of the vertebrae to be aligned. For that purpose, the top end 35 of the bone fastener 32 is provided with a hexagonally shaped circumference so that the bone fastener can be securely gripped by a fastening tool, such as a wrench, and the bone fastener screwed into the vertebrae. The bone fastener 32 may also be fastened to a vertebra by means other than a threaded connection as will be understood by those skilled in the art.

The bone fastener 32 also includes both a supporting portion 40 that is positioned at the top end 35 of the shank and a securing portion 37. The supporting portion 40 includes a spherical recess 41 in the embodiment of the invention illustrated in the drawings. The adjusting member 44 is supported by the supporting portion 40 of the bone fastener 32 in the spherical recess 41 of the supporting portion 40 and has a complementary spherical surface 45 where the adjusting member 44 is supported by the supporting portion 40 of the bone fastener.

The securing portion 37 of the bone fastener 32 comprises a threaded cavity for receiving the securing fastener 50 which is provided with threads 51 that secure the securing fastener to the threaded cavity. The adjusting member 44 has an opening 46 that extends through the adjusting member and is in registration with the threaded cavity of the securing portion 37 of the bone fastener 32.

From the foregoing description, it will be understood that the supporting portion 40 of the bone fastener 32 and the adjusting member 44 are configured so that the adjusting member 44 is supported by the supporting portion 40 of the bone fastener 32 for universal movement relative to the supporting portion of the bone fastener. Thus, the concave spherical recess 41 of the supporting portion 40 of the bone fastener and the convex spherical surface 45 of the adjusting member 44 allow for the adjusting member to be universally pivoted within spherical recess 41.

The adjusting member 44 includes an engaging surface 47 that, essentially, is flat and engages the underside 17 of the first portion 13 of the coupling member 12. As discussed in greater detail below, it is important that there be good contact between the engaging surface 47 of the adjusting member and the underside 17 of the first portion 13 of the coupling member 12. To provide such contact, any angularity that exists between the engaging surface 47 and the underside 17 of the coupling member when the bone fastener assembly is being secured to the coupling member 12 can be corrected by appropriate pivoting of the adjusting member 44 in the spherical recess 41 of the supporting portion 40 of the bone fastener 32. In this connection, as can be seen in FIG. 3, the adjusting member 44 is sized so that the engaging surface 47 of the adjusting member extends sufficiently beyond the terminal portion 42 of the supporting portion 40 of the fastener in the direction of the underside 17 of the coupling member 12 so that the terminal portion 42 is maintained out of contact with the underside 17 of the coupling member. Otherwise, good contact between the engaging surface 47 and the coupling member 12 would be compromised.

It can be seen from FIGS. 2 and 3 that the opening 46 in the adjusting member 44 extends from a first end at the engaging surface 47 of the adjusting member to a second end that abuts the threaded cavity of the securing portion 37 of the bone fastener. The second end of the opening 46 is larger than the first end of the opening so that the opening will remain in registration with the threaded cavity of the securing portion 37 of the bone fastener regardless of any anticipated adjustment of the adjusting member 44 in the spherical recess 41. In the embodiment of the invention illustrated in the drawings, the opening 46 has the shape of a frustrum of a cone. This arrangement insures that the securing fastener 50 will be able to pass through opening 46 and be secured within the threaded cavity in the securing portion 31 of the bone fastener 32 without interfering with any adjustment of the adjusting member 44.

The first portion 13 of the coupling member 12 of the appliance 10 includes an elongated aperture 18 in the top half 23 and the bottom half 24 of the coupling member 12 which enables the coupling member to be fastened to the bone fastener 32 through the instrumentality of the securing fastener 50. The securing fastener has a first end 52 that passes through aperture 18 and extends through the opening 46 in the adjusting member 44. The first end 52 of the securing fastener 50 is secured to the securing portion 37 of the bone fastener 32 by means of the threads 51 on the securing fastener and the threads in the cavity in the securing portion 37.

A second end 53 of the securing fastener 50 has a bearing surface 54 that bears against the topside 19 of the first portion 13 of the coupling member 12 of the appliance 10. The bearing surface 54 bears against the coupling member in opposition to the engaging surface 47 of the adjusting member 44 whereby the appliance 10 is securely fastened to the bone fastener 32. As can be best seen in FIGS. 1 and 3 (especially FIG. 3), at least part of the second portion 53 nests into a height of the coupling member (i.e., part does not stick out as shown in FIGS. 1 and 3). As noted above, any angularity between the underside 17 of the coupling member 12 and the engaging surface 47 of the adjusting member 44 will be corrected by appropriate pivoting of the adjusting member 44 in the spherical recess 41 of the supporting portion 40 of the bone fastener 32. However, in that instance because the securing fastener 50 will be aligned with the longitudinal axis of the shank 33 of the bone fastener, the securing fastener 50 will engage the coupling member 12 at an angle. To provide good contact between the bearing surface 54 and the coupling member 12 under such circumstances, the bearing surface 54 has a convex spherical configuration and the perimeter 21 of aperture 18 in the top half 23 of the coupling member 12 which engages the bearing surface 54 is provided with a complementary concave spherical surface. Similarly, the perimeter 20 of aperture 18 in the bottom half 24 of the coupling member 12 which also engages the bearing surface 54 is provided with a concave complementary concave spherical surface. Although the securing fastener 50 is depicted in the Figures with a slotted drive mechanism, other types of drive mechanisms, such as mechanisms familiar to those skilled in the art may be employed.

The invention, as illustrated in FIGS. 1 through 3, depicts the engaging surface 47 of the adjusting member 44 and the underside 17 of the coupling member 12 as being perpendicular to the longitudinal axis of the shank 33 of the fastener 32. However, rarely will that be case and, as indicated in the foregoing description of the invention, an angularity will exist between the underside 17 of the coupling member 12 and the longitudinal axis of the shank and that angularity will be compensated for by the adjusting member 44. Thus, in order to install the apparatus of the invention for the purpose of retaining a plurality of vertebrae in a desired spatial relationship, typically, a respective bone fastener 32 will be screwed into each of the vertebrae. With existing technology, it is not possible to attach the bone fasteners to the vertebrae so that no angularity exits between the mutually engaging surfaces of each of the bone fasteners 32 and respective coupling members 12; and as has been described above, the angularity is compensated for by the pivoting of each adjusting member 44 in the spherical recess 41 of a respective supporting portion 40 of a bone fastener 32. This adjustment places the engaging surface 47 of the adjusting member in a parallel, rather than angular, relationship with the underside 17 of the coupling member 12. The opening 46 in the adjusting member 44 is sufficiently large that such adjustment of the adjusting member 44 will not place the opening 46 out of registration with the threaded cavity in the securing portion 37 of the bone fastener. Consequently, the securing fastener 50 is able to pass through the opening 46 in the adjusting member 44 and be secured in the threaded cavity in the securing portion 37 of the bone fastener.

For aligning the vertebrae in their desired orientation, the fact that the aperture 18 is elongated allows the distance between the fixation rod 26 and the bone fastener assembly 30 to be adjusted. Once the proper distance is established, the securing fastener 50 is tightened in the threaded cavity in the securing portion 37 of the bone fastener. Tightening of the securing fastener 50 will cause the engaging surface 47 of the adjusting member 44 to come into contact with the underside 17 of the coupling member 12 whereby the adjusting member 44 will pivot in the spherical recess 41 of the supporting portion 40 of the bone fastener 32, resulting in full contact between the engaging surface 47 and the underside 17 of the coupling member 12. Additionally, the convex bearing surface 54 of the securing fastener 50 will engage and bear on the complementary concave surfaces of the perimeters 20 and 21 of the aperture 18. In the embodiment of the invention shown in the drawings, the convex bearing surface 54 of the securing fastener 50, the surface 45 of adjusting member 44, spherical recess 41 and the concave spherical surfaces 20 and 21 all have a common center of rotation so that forces applied by the securing fastener are normal to the engaging surfaces of the various elements of the bone fastener assembly and appliance. This procedure is carried out with each bone fastener assembly and a respective coupling member until the apparatus is completely secured so as to retain the vertebrae in a desired spatial relationship. Tightening of the securing fastener 50 also will cause the yoke 15 to compress the grommet 25 and securely attach the coupling member 12 to the rod 26.

Although the invention has been described in relation to the use of a rigid rod 26 so that an essentially immovable stabilizing apparatus is provided, rods may be employed that possess a degree of flexibility such that limited movement of the apparatus can take place once it is installed. Additionally, the appliance to which the bone fastener assembly of the invention is applied can be other than a rod and coupling member. For example, a plurality of the bone fastener assemblies attached to bone bodies can be secured directly to a plate provided with cooperating apertures and the bone bodies to which the assemblies are attached thereby retained in a desired spatial relationship.

The foregoing description and discussion of the invention has been presented for purposes of illustration and to facilitate the presentation of aspects of the invention. The foregoing is not intended to limit the invention to those aspects. Although the description of the invention has included discussions of certain variations and modifications, other variations and modifications may become apparent to those skilled in the art and it is intended that the scope of the invention as set forth in the claims below be inclusive of such variations and modifications.

What is claimed is:

1. An apparatus for use in retaining bone bodies in a desired spatial relationship, the apparatus including:
    an elongated member for extending adjacent to the bone bodies;
    a coupling member for engagement with and gripping of the elongated member; the coupling member including first and second clamp portions, each clamp portion having a first, curved segment extending partially around the elongate member for retaining the elongate member and a second, flat segment having a elongate aperture extending therethrough;
    a monolithic bone fastener having a threaded lower attaching portion for attaching the bone fastener to one of the bone bodies and an upper portion, the upper portion including a hexagonally-shaped outer circumference for engagement by a tool, a concave spherical recess located at the top-most end of the monolithic bone fastener and located radially within the hexagonally-shaped outer circumference, and a threaded recess extending from and being relatively below the concave spherical recess;
    an annular adjusting member, separate from the coupling member and the bone fastener, having a convex engaging surface complementary to the recess at the top-most end of the monolithic bone fastener located on a lower portion of the adjusting member and extending into the concave recess radially within the hexagonally-shaped outer circumference, a flat engaging surface located on an upper portion of the annular adjusting member and engaged with the flat segment of one of the clamp portions of the coupling member with the coupling member spaced away from the monolithic bone fastener and the elongated member also spaced away from the monolithic bone fastener, and a conical opening extending through the adjusting member; and
    a threaded securing fastener including a first portion extending through the elongate apertures of the flat segments of the first and second clamp portions, extending through the opening in the adjusting member and extending in threaded engagement into the threaded recess of the bone fastener, and a second portion bearing against the flat segment of the other of the clamp portions of the coupling member and being sized to at least partially nest into a height of the coupling member, the securing fastener may be located anywhere along the elongate slot to provide force to the coupling member cause the first and second clamp portions to retain the elongate member relative to the bone fastener, including a height location relative to the bone fastener, without the elongate member or the coupling member engaging the bone fastener and without structure extending beyond the height location of the elongate member.

2. The apparatus as set forth in claim 1 wherein the adjusting member is sized so that the engaging surface of the adjusting member extends radially beyond the upper portion of the bone fastener to prevent contact between the bone fastener and the coupling member.

3. The apparatus as set forth in claim 1 wherein the opening in the adjusting member extends from a first end at the engaging surface of the adjusting member to a second end that abuts the threaded cavity in the securing portion of the bone fastener, and the second end of the opening is larger than the first end of the opening in the adjusting member.

4. The apparatus as set forth in claim 1, wherein the coupling member includes a spherical gourmet located within the first, curved segments of the first and second clamp portions for engaging the elongate member.

5. The apparatus as set forth in claim 1, wherein the second portion of the threaded securing fastener has a convex spherical configuration and a perimeter of the elongate aperture in the first clamp portion has a complementary concave profile.

* * * * *

UNITED STATES PATENT AND TRADEMARK OFFICE
CERTIFICATE OF CORRECTION

PATENT NO. : 7,578,833 B2  Page 1 of 1
APPLICATION NO. : 11/011794
DATED : August 25, 2009
INVENTOR(S) : Robert S. Bray It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 764 days.

Signed and Sealed this

Fourteenth Day of December, 2010

David J. Kappos
*Director of the United States Patent and Trademark Office*